United States Patent [19]

Ingham

[11] Patent Number: 5,256,134
[45] Date of Patent: Oct. 26, 1993

[54] CONFORMABLE BANDAGE

[75] Inventor: Philip Ingham, Hebden Bridge, United Kingdom

[73] Assignee: Smith & Nephew plc, United Kingdom

[21] Appl. No.: 663,875

[22] PCT Filed: Sep. 11, 1989

[86] PCT No.: PCT/GB89/01065
§ 371 Date: Mar. 6, 1991
§ 102(e) Date: Mar. 6, 1991

[87] PCT Pub. No.: WO90/02539
PCT Pub. Date: Mar. 22, 1990

[30] Foreign Application Priority Data

Sep. 9, 1988 [GB] United Kingdom ............... 8821223
Jan. 10, 1989 [GB] United Kingdom ............... 8900437

[51] Int. Cl.$^5$ ..................... A61F 5/04; A61F 13/00
[52] U.S. Cl. ................... 602/8; 66/169 R; 66/170; 66/195; 66/202; 428/230; 428/231; 428/245; 428/253; 602/5
[58] Field of Search ............... 428/259, 260, 230, 254, 428/288, 289, 290, 231, 245, 253; 602/5, 8, 44, 45, 76; 66/169 R, 190, 195, 202, 170; 128/90, 89 R, 155, 156

[56] References Cited

U.S. PATENT DOCUMENTS

| 2,711,168 | 6/1955 | Brickman et al. | 602/5 |
|---|---|---|---|
| 2,960,984 | 11/1960 | Parker | 602/44 |
| 3,135,258 | 6/1964 | Billings et al. | 602/5 |
| 3,332,416 | 7/1967 | Brickman et al. | 602/8 |
| 3,881,473 | 5/1975 | Corvi et al. | 602/44 |
| 4,134,397 | 1/1979 | Gianakakos et al. | 602/5 |
| 4,323,061 | 4/1982 | Usukura | 602/8 |
| 4,411,262 | 10/1983 | von Bonin et al. | 428/260 |
| 4,572,171 | 2/1986 | Wegner et al. | 428/282 |
| 4,638,648 | 1/1987 | Gajjar | 66/193 |
| 4,668,563 | 5/1987 | Buese et al. | 428/230 |
| 4,745,912 | 5/1988 | McMurray | 428/254 |

FOREIGN PATENT DOCUMENTS 1165201 3/1964 Fed. Rep. of Germany .
2082214A 8/1980 United Kingdom .

OTHER PUBLICATIONS

Textile Institute, Textile Terms and Definitions, p. 101, etc., Eighth Edition, 1986.

Primary Examiner—George F. Lesmes
Assistant Examiner—James D. Withers
Attorney, Agent, or Firm—Rosenman & Colin

[57] ABSTRACT

A warp knitted fabric is described in which each individual wale contains stitches formed from both elastic and inelastic yarn. The fabric is extensible in the direction of the wales and may be used as a substrate in an orthopaedic splinting bandage. Orthopaedic splinting bandages are also described which comprise the warp knitted fabric coated with a hardenable resin such as an isocyanate terminated propolymer. The lengthwise extensibility of the substrate makes the uncured bandage conformable during application to the body.

8 Claims, No Drawings

CONFORMABLE BANDAGE

The present invention relates to a knitted fabric which is suitable for use as a substrate in hardenable orthopaedic splinting bandages. The present invention also relates to an orthopaedic bandage comprising a resin-coated fabric substrate which has improved conformability.

Conventional orthopaedic splinting bandages for use in the treatment of bone fractures or other conditions requiring immobilization of part of the body are formed from a substrate impregnated with a substance which hardens to a rigid structure after wrapping the bandage around the body. Traditionally Plaster of Paris has been used but more recently certain plastics have gained acceptance as replacements for Plaster of Paris. Such new bandages are lighter, waterproof and permeable to X-rays. Substrates for use with these plastics have included glass fibre fabrics such as those described in U.S. Pat. Nos. 4,502,479, 4,609,578, 4,668,563 and 4,323,061.

One disadvantage of substrates including glass fibres is that the casts formed from them can become brittle and break down during wear and hence need to be replaced before healing is complete. A second disadvantage is that during cast removal irritating glass dust or fibres may be generated. These disadvantages would be mitigated by using a substrate which gave a durable cast and did not give rise to irritating fibres on cast removal. However, heretofore such substrates have lacked the conformability and cast strength found when using glass fibre substrates.

A knitted fabric has now been made containing individual wales knitted from elastic yarn and inelastic yarn and when using this fabric as a substrate a bandage is achieved which has good conformability compared to those employing existing fabric substrates. Even more surprisingly the cast formed using this novel substrate does not slow a loss of strength compared to a cast which employs a glass fibre substrate. A further advantage of this fabric is that it is found to possess surprisingly good dimensional stability that is it has little or no propensity to curl which aids processing such as coating.

Although the presence of wales which are knitted from both elastic and inelastic yarns is most useful in substrates which do not contain glass fibres it is envisaged that the same construction could be used with glass fibres to advantage.

The present invention provides a warp knitted fabric which contains wales which are knitted from both elastic and inelastic yarns.

The warp knitted fabric of the invention is an elastic fabric that is to say that it possesses recoverably extensibility in a direction parallel to the wales which contain the elastic yarn. An elastic yarn is a yarn formed form an elastomer. An elastomer may be defined as a rubber or polymer which has high extensibility together with rapid and substantially complete elastic recovery. Suitable elastic yarns for use in the invention include those which have an elongation at break of greater than 100% and more suitably, greater than 300%.

The warp knitted fabric of the invention is described herein with reference to its use as a substrate in an orthopaedic bandage. It is envisaged that the fabric may be used in other applications where its elastic properties may be employed to advantage, for example in bandages and clothing.

In one favoured aspect therefore the present invention provides a warp knitted fabric suitable for use as a substrate in a resin coated, water hardenable orthopaedic splinting bandage which fabric contains wales which are knitted from both elastic and inelastic yarns.

In a second aspect the present invention provides a conformable hardenable orthopaedic sprinting bandage comprising a warp knitted fabric substrate coated with a curable resin which fabric substrate contains wales knitted from both elastic and inelastic yarns. Most suitably the resin is a water curable resin so that the bandage is one which hardens after being exposed to water.

It is clear from the above that each individual wale is knitted from both elastic and inelastic yarns. The fabric normally has a planar surface.

The orthopaedic splinting bandages of the present invention possess lengthwise extensibility by virtue of the presence of elastic yarns knitted into the wales of the fabric. Suitable elastic yarns include those formed from natural rubber or a synthetic elastomer such as polyisoprene, polybutadiene, copolymers thereof, elastomeric ethylene-propylene copolymers and thermoplastic elastomers including block copolymers of styrene and butadiene or isoprene or an elastic polyurethane yarn. A particularly preferred elastic yarn is a spandex yarn, that is a polyurethane yarn for example Lycra yarn (Trade mark).

The inelastic yarns of the knitted substrate may be formed from yarns which include yarns formed from polypropylene, polyester, polyamide, polyethylene, cotton viscose. A preferred yarn is polyester yarn, including multifilament or monofilament polyethylene terephthalate yarn.

A wale when used herein- means a column of loops along the length of the fabric. In the fabric of the invention some of the loops in each wale are formed from either elastic yarn and some formed from inelastic yarn and are preferably knitted in a repeating pattern along the wale. When not being knitted as a loop the yarn mislaps until required for knitting again. The non-knitted yarn may be laid into the knitted stitches or may be allowed to float on the surface of the fabric. Typically in a 4 bar warp knitted fabric there may be 2 polyester stitches to 1 elastomer stitch or vice versa. This is unlike previously known elastic fabrics where either all the loops of the wales are formed from elastic yarn or elastic yarn is incorporated as an inlay along a wale formed from inelastic yarn. This new manner of knitting surprisingly gives the additional advantage of dimensional stability, shown by lack of inward curl, over a wider range of mesh dimensions.

Suitably the lengthwise extension of the substrate that is in the direction of the wales, may be from 15 to 200%, more suitably 25 to 160% and preferably 50 to 150%. The degree of extension may be varied according to the type of elastic yarn chosen but the above ranges are suitable for substrates used in orthopaedic bandages.

When coated with resin the lengthwise extension can be at least 25%, more suitably at least 40% and preferably at least 50%. The upper limit to lengthwise extensibility can be 60%, more suitably 70% and preferably at least 80%.

Suitably the widthwise extension of the substrate may be from 20 to 150%, more suitably 20 to 100%, most suitably 25 to 60% and preferably 30 to 50% for example 45%.

The elastic yarns in the substrate appear to cause the substrate to return to its original length after stretching and so facilitate conformability of the substrate to the patient's body. The bandages were observed to conform easily to various shaped formers made to represent parts of the body.

Suitably the knitted substrate has a low power, that is the force required to stretch the substrate for a given percentage extension. If this power is low then this will help to prevent constriction of the patient's limb after the bandage has been applied.

The lengthwise extension may be measured using an Instron Tensile Testing Machine. A 10 cm length of substrate may be clamped in the jaws of the machine and the jaws separated at constant speed. A conventional stress-strain curve for the substrate may be recorded. The extension at a given load and the load required to give a given extension can be calculated from the curve for the substrate under test.

For the best shelf life of the resin coated substrates, the elastic yarn used in the substrate must be compatible with the resin with which it is coated. Suitable compatible elastic yarns may be identified by forming a bandage incorporating the elastic yarns and coating with the resin and ageing in a sealed container for 12 weeks at 55° C. If at the end of this time the bandage may be used to form a satisfactory cast then the elastic yarn is suitable particularly for use in conjunction with the resin. The unsuitability of some elastic yarns may be overcome by means of coating or wrapping the yarn with other inert materials such as cotton or nylon yarn. For example elastic polyurethane yarns may be wrapped in cotton or nylon.

Suitably the substrate may have a thickness of from 0.375 mm to 4.0 mm, more suitably will be 0.50 mm to 3.00 mm thick and preferably 1.00 mm to 2.00 mm thick, for example 1.50 mm.

Suitably the knitted substrate may have a weight per unit area when relaxed of from 50 to 500 $gm^{-2}$ more suitably may have a weight of from 100 to 350 $gm^{-2}$, and preferably a weight of between 150 and 220 $gm^{-2}$ for example 170 g, 175, 180, 185 and 190 $gm^{-2}$.

Suitably the fabric may be produced on a warp knitting machine or on a crochet knitting machine. The fabric is a warp knitted fabric comprising chain or pillar stitches linked by under-lapped inlay threads. In the fabric of the invention the elastic yarn is incorporated in the pillar stitch so as to give the lengthwise stretch.

Normally when producing a pillar or chain stitch in a warp knitted fabric the same yarn guide always overlaps the same needle. This produces chains of loops in unconnected wales which are then connected together by underlaps of yarn from second or other guide bars to form the fabric. When the elastic yarn is present at least two yarn guides are used to produce each pillar stitch. The first guide feeds the in-elastic yarn to the needle which knits one or more courses before being withdrawn to let in the second guide which feeds in the elastic yarn to the needle which again knits for one or more courses before the second guide withdraws and the first guide is let in. This cycle is repeated as knitting proceeds. The knitting provides a stable fabric with a reduced tendency to curl.

The resins used in the orthopaedic bandage of the invention may be any curable resin which will satisfy the functional requirements of an orthopaedic cast. The preferred resins are those cured with water or moisture and include the resins described in U.S. Pat. Nos. 4,667,661, 4,502,479, 4,574,793, 4,433,680, 4,427,002, 4,411,262, 3,932,526, 3,908,644, 3,630,194, in German Offenlengungsschrift No. 2651089 and in European Patent Applications Nos. 35517, 57988, 86621 and 94222.

Aptly the resin used to coat the fabric substrate may be a water curable isocyanate terminated prepolymer system. Among suitable prepolymer systems are those identified in U.S. Pat. Nos. 4,411,262, 4,427,002, 4,433,680 and 4,574,793. Particularly preferred are those systems disclosed and claimed in U.S. Pat. Nos. 4,427,002 and 4,574,793 the disclosures of which are incorporated herein by cross-reference.

Suitably the bandage may be formed by coating or impregnating the substrate with the resin in the manner described in those patents, particularly in U.S. Pat. No. 4,427,002.

Suitably the weight of resin on the substrate is from 150 to 650 $gm^{-2}$ and mare suitably from 150 to 500 $gm^{-2}$, most suitably a weight of 200 to 450 $gm^{-2}$ and preferably 225 to 450 $gm^{-2}$ most preferably between 250 to 400 $gm^{-2}$. The weight of resin may be chosen so that suitably 40 to 60% of the total weight of the bandage is resin and more suitably 55 to 60% of the total weight. Thus if the fabric weight is 180 gsm and the resin coating is 55–60% of the bandage then the weight of resin taken is 220–270 g.

The formed bandages may be packaged by heat sealing in waterproof pouches such as those formed from metal foil polyethylene laminates or polyethylene pouches.

In use the bandages may be brought into contact with water and wrapped around the injured part of the body. The setting bandage has a working time which is sufficient to allow the bandage to be positioned on the limb and a set time which is the tine taken for the cast to become rigid. Apt working times are 1 to 6 minutes and apt set times are 5 to 30 minutes.

The cast incorporating the substrate of the invention is readily removable by conventional means such as by cutting with a conventional circular saw. Large casts may be removed using a single cut along the length of the cast which is not always achievable with fibre glass substrate casts.

The build-up of strength in the cast was assessed by wrapping the resin-coated substrate round a former to make a cylinder. The former is removed and the cylinder wall clamped in a Instron Tensile Testing machine so as to measure diametral compression and extension forces. The machine is adapted so that the moving clamp would oscillate between positions 2.5 mm from the rest position. The force required to deform the cast as it set over a period of time is measured. The results were recorded an a chart recorder. A bandage formed according to Example 2, which was 4 layers thick, was tested in comparison with a conventional glass fibre based bandage using cylinders formed of 5 layers of bandage. The bandage according to the invention was greater in strength to the glass fibre bandage both on initial setting and after 24 hours.

|  | Rigidiy (kg/cm width) Time after initiation of set | | |
| --- | --- | --- | --- |
|  | 15 mins | 30 mins | 24 hr |
| Bandage of Example 2 (4 layers) | 2.7 | 3.4 | 5.3 |
| Glass fibre-based bandage (5 layers | 2.1 | 2.65 | 4.5 |

For the following examples the knitting machine has 12 needles per inch and is threaded half sett. The knitting notation is an English notation.

EXAMPLE 1

Preparation of substrate

A substrate was prepared by knitting together elastic polyurethane yarns and polyester yarns. The elastic polyurethane yarns were formed from a segmented polyurethane and are available as Lycra spandex yarns. The yarns had a weight per unit length of 156 dtex. The yarns may be wrapped in nylon or cotton or other yarns. The polyester was a multifilament polyethylene terephthalate with a weight per unit length of 1100 dtex.

The knitting pattern was as follows:

| Bar 1 | 1-0/0-1/1-1 | (Polyester yarn) |
|---|---|---|
| Bar 2 | 0-0/1-1/1-0 | (Lycra yarn) |
| Bar 3 | 3-3/2-2/3-3/0-0/1-1/0-0 | (Polyester yarn) |
| Bar 4 | 0-0/1-1/0-0/3-3/2-2/3-3 | (Polyester yarn) |

The machine was 12 gauge and each guide bar was threaded half sett.

The fabric so knitted has 30 to 34 wales/10 cm width and 35 to 43 courses/10 cm. The fabric was knitted at a 10 cm width. The fabric has a weight per unit area of 200 gm$^{-2}$.

The knitted fabric has an extension in the width direction of 80% and extension in the lengthewise direction of 50% (approx.).

This fabric is suitable for use as a substrate in an orthopaedic splinting bandage.

EXAMPLE 2

Preparation of Bandages

A water curable polyurethane resin system comprising a polyurethane prepolymer described in U.S. Pat. No. 4,574,793 as prepolymer A and containing methane sulphonic acid as stabiliser and bis (2,6 dimethyl morpholino) diethyl ether as catalyst is coated onto a knitted fabric described in Example 1 using the process described in U.S. Pat. No. 4,427,002. The weight of the resin applied is 240 gm$^{-2}$ which means that the resin forms 55% of the weight of the bandage. The coated bandage had a lengthwise extension of 25% approximately.

The bandage strip is cut into 3 meter lengths and spooled onto rolls. The bandage rolls are then placed into pouches which are heat sealed to prevent exposure of the contents to moisture.

A bandage is made into a cast by dipping the bandage roll in water and wrapping around a body member.

EXAMPLE 3

Preparation of Substrate

A fabric was prepared by knitting together elastic polyurethane yarns and polyester yarns. The elastic polyurethane yarns are formed from a segmented polyurethane and are available a-s Lycra spandex yarns and may be wrapped in nylon or cotton. The yarns had a weight per unit length of 156 dtex. The polyester was a multifilament polyethylene terephthalate with a weight per unit length of 1100 dtex.

The knitting pattern was as follows:

| Bar 1 | 1-1/1-1/1-0/0-0/0-0/0-1 | (Lycra fibre) |
|---|---|---|
| Bar 2 | 1-0/0-1/1-1/1-0/0-1/1-1 | (Polyester fibre) |
| Bar 3 | 3-3/2-2/3-3/0-0/1-1/0-0 | (Polyester fibre) |
| Bar 4 | 0-0/1-1/0-0/3-3/2-2/3-3 | (Polyester fibre) |

The machine was 12 gauge and each guide bar was threaded half sett.

The fabric knitted according to this pattern has a weight per unit area of 175 gm$^{-2}$, 30 to 34 wales/10 cm width and 35 to 43 courses/10 cm length.

This fabric is suitable for use in an orthopaedic splinting bandage.

EXAMPLE 4

Preparation of Bandages

A bandage was prepared using the fabric described in Example 3 as the substrate in the manner described in Example 2.

EXAMPLE 5

Preparation of Fabric

A fabric was prepared by knitting together an elastic polyurethane yarn and polyester yarns. The elastic polyurethane yarn was formed from a segmented polyurethane available as a Lycra spandex yarn. The yarn had a weight per unit length of 156 dtex. The fibres may be wrapped in nylon or cotton or other suitable yarns. The polyester was a multifilament polyethylene terephthalate with a weight per unit length of 1100 dtex.

The knitting pattern was as follows:

| Bar 1 | Polyester | 1-0/0-1/1-1 |
|---|---|---|
| Bar 2 | Lycra | 0-0/1-1/1-0 |
| Bar 3 | Polyester | 3-3/2-2/3-3/0-0/1-1/0-0 |
| Bar 4 | Polyester | 0-0/1-1/0-0/3-/2-2/3-3 |

The machine was 12 gauge and each guide bar was threaded half sett.

The knitting machine was set to knit 4.0 courses/cm. In the wales, the knitting was such that the Lycra stitch was the first stitch after the inlay crossover. The repeat pattern in the pillar stitch was 2 polyester:1 Lycra stitch.

The knitted fabric has an extension in the width direction of 75–80% and the extension in the lengthwise direction is 50% (approx).

The fabric is suitable for use as a substrate in an orthopaedic splinting bandage.

EXAMPLE 6

Preparation of Fabric

A fabric was prepared in a similar manner to and from the same yarns as described in Example 5 except that Bar 1 carried the elastic yarn and Bar 2 carried a polyester yarn. In this construction the pillar stitch repeat is now 2 Lycra stitches:1 polyester stitch. The polyester stitch is positioned on the inlay cross-over. When not knitting the guide bar 2 in-lap the polyester yarn inside the Lycra stitches.

The fabric has similar characteristics to that prepared as in Example 5.

EXAMPLE 7

Preparation of Fabric

A fabric was prepared from similar materials as those described in Example 5.

The knitting pattern was as follows:

| Bar 1 | Polyester | 0-0/1-1/1-0 |
|---|---|---|
| Bar 2 | Lycra | 1-0/0-1/1-1 |
| Bar 3 | Polyester | 3-3/2-2/3-3/0-0/1-1/0-0 |
| Bar 4 | Polyester | 0-0/1-1/0-0/3-3/2-2/3-3 |

The machine was 12 gauge and each guide bar was threaded half sett.

In this construction the pillar stitch repeat is two Lycra stitches:1 polyester stitch. The polyester stitch is positioned on the inlay cross-over point. When not knitting the guide bar 2 allows the polyester yarn to float on the surface of the fabric rather than to inlay up the pillar stitch inside the Lycra stitches.

The fabric has similar characteristics to that prepared in Example 5.

EXAMPLE 8 TO 11

Preparation of Fabric

Suitable fabrics are prepared by using polypropylene yarn with the same knitting patterns described in Examples 1, 5, 6 and 7. The polypropylene yarn used is a 70 filament yarn of weight per unit length of 470 dtex.

EXAMPLE 12

Preparation of Bandages

A resin was formed from Isonate 143L (47.8%), Isonate 240 (14.7%), Voranol (3.5%), propylene glycol (31.9%), antifoam (0.3%), methane sulphonic acid (0.03%) and bis (2.6-dimethyl morpholino-N-ethyl) ether (1.8%).

The resin was spread at 54% by weight of the weight of the total bandage onto the substrate described in Example 1 (10 cm × 10 cm) using a hopper and doctor knives in a conventional manner under nitrogen. The bandage was wound onto a core to form a roll and sealed into an aluminium foil pouch under argon.

A bandage was removed from a pouch and immersed in water. The bandage was squeezed three times under water to ensure wetting, removed, shaken and applied to a mandrel. The bandage provided a suitable cast.

EXAMPLE 13 TO 20

Preparation of Bandages

A resin as described in Example 12 was applied to fabrics described in Examples 3, 5 to 11 by the process described in Example 12. The coated substrates provided suitable bandages for forming casts.

I claim:

1. A conformable, hardenable, orthopaedic splinting bandage comprising a warp knitted fabric substrate coated with a curable resin wherein said fabric substrate contains individual wales, each individual wale comprising a repeating pattern of loops knitted from an elastic yarn and an inelastic yarn, said elastic yarn or inelastic yarn mislapping when not knitted to form said loops.

2. A bandage as claimed in claim 1 wherein said curable resin is a water curable resin.

3. A bandage as claimed in claim 2 wherein said water curable resin is an isocyanate terminated prepolymer.

4. A bandage as claimed in claim 1 wherein in each wale of the fabric substrate, the elastic or inelastic yarn which is not being knitted as a loop is laid into the knitted stitches of a yarn which is being knitted as a loop.

5. A bandage as claimed in claim 1 wherein in each wale of the fabric substrate, the yarn which is not being knitted as a loop is allowed to float on the surface of the fabric.

6. A bandage as claimed in claim 1 wherein the repeating pattern along the wale is 2 inelastic yarn loops to 1 elastic yarn loop or 2 elastic yarn loops to 1 inelastic yarn loop.

7. A bandage as claimed in claim 1 wherein the coated bandage has an extension of at least 25%.

8. A bandage as claimed in claim 1 wherein the substrate has a weight per unit area of 100 to 350 $gm^{-2}$ and the resin is 40 to 60% of the total weight of the bandage.

* * * * *